US00PP37403P2

(12) United States Plant Patent
Hansen

(10) Patent No.: US PP37,403 P2
(45) Date of Patent: May 5, 2026

(54) LEUCANTHEMUM PLANT NAMED 'Dream Big'

(50) Latin Name: ***Leucanthemum* x *superbum* (Bergmans ex J.W. Ingram) D.H.Kent**
Varietal Denomination: Dream Big

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,831

(22) Filed: Sep. 23, 2025

(51) Int. Cl.
*A01H 6/14* (2018.01)
*A01H 5/02* (2018.01)

(52) U.S. Cl.
USPC ..... Plt./285

(58) Field of Classification Search
USPC ..... Plt./285
See application file for complete search history.

(56) References Cited

U.S. PATENT DOCUMENTS

PP35,456 P2 * 11/2023 Hansen ..... Plt./285

* cited by examiner

*Primary Examiner* — Karen M Redden

(57) ABSTRACT

The new Shasta daisy plant, *Leucanthemum* 'Dream Big', is a sturdy dense plant with large, dark-green, serrated foliage and stiff stems. The numerous large semi-double inflorescences produce two to three rows of overlapping, horizontal, white, ray florets and a center capitulum with disk florets that are golden yellow. The new plant is useful in the landscape as a long-flowering border, in mass, as accent plants and containerized for patio or indoor use, or as a cut flower.

1 Drawing Sheet

Botanical classification: *Leucanthemum* x *superbum* (Bergmans ex J. W. Ingram) D. H. Kent.
Variety denomination: 'Dream Big'.

STATEMENT REGARDING PRIOR DISCLOSURES UNDER 37 CFR 1.77(B)(6)

The first offer for sale anywhere in the world was made by Walters Gardens, Inc. to Prides Corner Farms on Oct. 11, 2025. Walters Gardens, Inc. obtained the new plant and all information about the new plant directly from the inventor. No plants of *Leucanthemum* 'Dream Big' have been sold or offered for sale, in this country or anywhere in the world, nor has any disclosure of the new plant been made, more than one year prior to the filing date of this application, and such sale or disclosure within one year was either derived directly or indirectly from the inventor.

BACKGROUND OF THE INVENTION

The original *Leucanthemum* x *superbum*, or Shasta daisies, were bred by Luther Burbank in the late 1800's as a cross between *Leucanthemum maximum* (Ramond) DC. with *Leucanthemum vulgare* (Vaill.) Lam., *Leucanthemum lacustre* (Broth.) Samp. and *Nipponanthemum nipponicum*. The new plant, *Leucanthemum* 'Dream Big' originated from a planned breeding program of the inventor at a wholesale perennial nursery in Zeeland, MI, USA. The new *Leucanthemum* was a single plant selected from a group of seedlings from a cross on Jul. 6, 2021, between the proprietary unreleased, unnamed proprietary hybrid known only by the breeder code 20-11-1 (not patented) as the female parent and the proprietary unreleased, unnamed proprietary hybrid known only by the breeder code 20-11-5 (not patented) as the male parent. The seeds were harvested on Sep. 1, 2020. The individual selected plant that eventually became 'Dream Big' was first evaluated in the summer of 2022 and given the breeder number 21-14-14 through the subsequent evaluations.

The present invention relates to a new and distinct cultivar of Shasta daisy botanically known as *Leucanthemum* x *superbum* and hereinafter referred to by the cultivar name 'Dream Big' or the new plant.

Asexual reproduction of the new cultivar by division at the same nursery in Zeeland, MI beginning in the summer of 2022 has demonstrated that the new cultivar reproduces true to type with all the characteristics of the original plant retained through successive generations of asexual propagation. The new plant has since been asexually propagated by basal shoot tip cuttings and sterile shoot tip tissue culture.

BRIEF SUMMARY OF THE INVENTION

The new plant is most closely compared to: 'Becky' (not patented), 'Daisy Duke' U.S. Plant Pat. No. 21,914, 'Marshmallow' U.S. Plant Pat. No. 33,878, 'Snowcap' (not patented), and 'Spoonful of Sugar' U.S. Plant Pat. No. 28,760.

'Becky' has a taller habit and has smaller inflorescences without lateral branching. 'Daisy Duke' is slightly shorter in habit with smaller inflorescences without lateral branching. 'Marshmallow' has a much shorter habit with narrower and more numerous ray florets. 'Real Snowball' has a shorter more mounded habit, and smaller inflorescences over a longer flowering season. 'Snowcap' has a shorter habit and smaller inflorescences. 'Spoonful of Sugar' has a much shorter habit and larger inflorescences.

The female and male were taller with weaker stems and shorter lateral branching at the end of the stems.

*Leucanthemum* 'Dream Big' differs from all cultivars known to the inventor in the following combined traits:

1. Sturdy, dense, upright, mounded plants with large, dark-green, serrated foliage and stiff stems;
2. Large semi-double inflorescences with two or three rows of overlapping white ray florets;
3. Center disk florets of golden yellow;
4. Multiple lateral branches.

BRIEF DESCRIPTION OF THE PHOTOGRAPHS

The photographs of 'Dream Big' demonstrate the overall appearance and landscape qualities of the new plant, including the unique traits planted in a full-sun trial garden in Zeeland, Michigan. The colors are as accurate as reasonably possible with color reproductions. Ambient light spectrum, source, direction, and temperature may cause the appearance of minor variations in color.

DETAILED BOTANICAL DESCRIPTION

Figure 1:
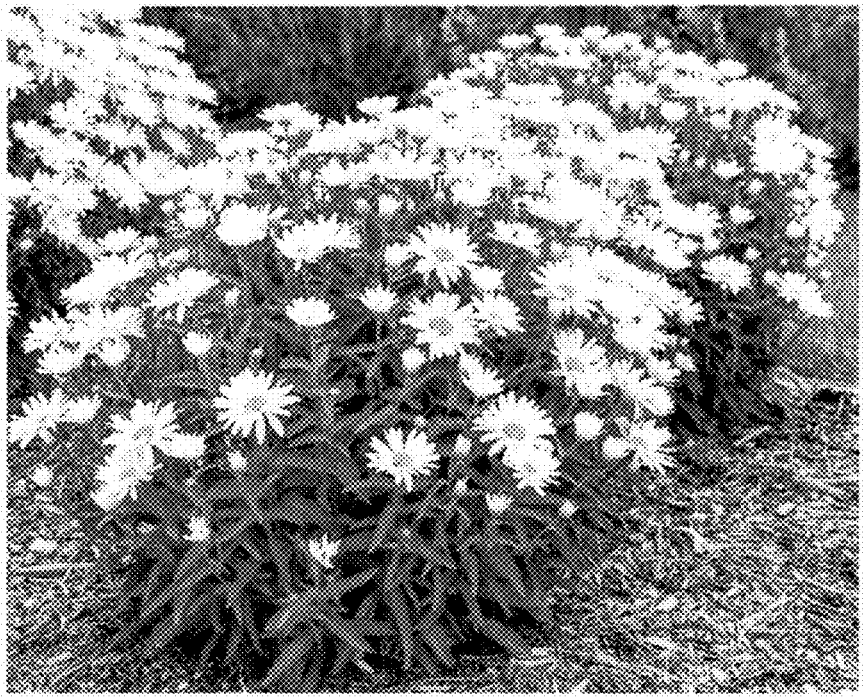
FIG. 1 shows a two-year-old new plant at early flowering with inflorescences covering the plant from nearly top to ground.
Figure 2:
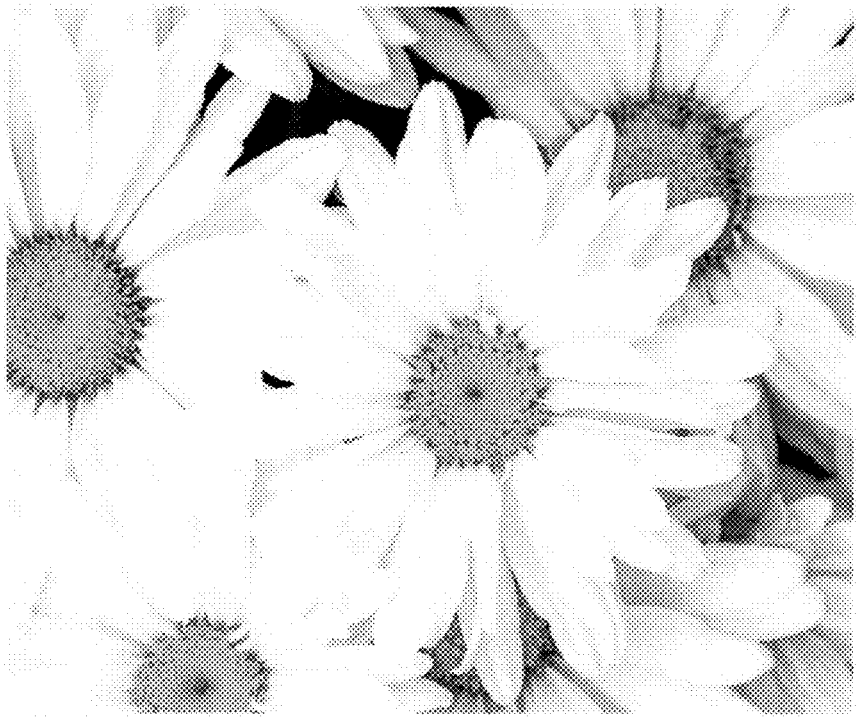
FIG. 2 shows a close-up of some inflorescences.

The following descriptions and color references are based on the 2015 edition of The Royal Horticultural Society Colour Chart except where common dictionary terms are used. The new plant has not been observed in all possible environments and conditions. The phenotype of *Leucanthemum* 'Dream Big' may vary with different growing conditions such as changes in temperature, light intensity, water availability, and nutrition, but without change in the genotype.

The plants used for description purposes were three-year-old and were grown in Zeeland, MI in a full-sun, loamy-sand trial plot environment with supplemental water and limited fertilizer as needed and also a partially-shaded greenhouse. Summer temperatures range from night lows of about 10° C. to daytime highs of about 34° C. Measurements and numerical values represent ranges of trial plants.

Botanical classification: *Leucanthemum* x *superbum;*

Parentage: Female parent is 20-11-1, male parent is 20-11-5;

Habit: Herbaceous perennial with about 50 to 80 branched stems arising from rhizome base; each stem having three to eight inflorescences each; about 65 cm tall and to about 82 cm across with rounded top;

Roots: Fibrous, thin, heavily branched; root color nearest RHS 155D depending on soil type;

Propagation: Tip cuttings or tissue culture; about two weeks to produce roots from cutting; about 6 to 8 weeks following vernalization to finish to flower in a 3.8-liter pot depending on the season;

Stems: About 50 to 80 main stems per plant; strong; mostly upright; canaliculated; hispidulous; terete, hollow in distal portion; 9.0 mm diameter at base; to 65 cm tall; about 9 nodes before terminal inflorescence in the lower 36.5 cm; average internode length about 3.3 cm; with two to eight inflorescences;

Stem color: Proximally between RHS 146D and RHS 144B, distally nearest RHS 146B with ridges nearest RHS 148C;

Axillary branches: Four to eight; extending above main inflorescence; between 14 to 31 cm long and 2.5 to 4 mm diameter; upright to angles of about 30° or less from main stem;

Axillary branch color: Between RHS 146B and RHS 146A with ridges nearest RHS 146C;

Leaves: Oblanceolate to spatulate; apex acute; proximal leaf bases petiolate and attenuate, with cauline leaf bases sessile, truncate to clasping; alternate; glabrous adaxial and abaxial; margin serrate and micro-ciliolate with average about eleven teeth per side, and size average about 2 mm long and 3 mm wide; proximal leaves to about 29 cm long and 5.5 cm wide, lower cauline leaves to about 16 cm long, 3.5 cm wide near middle; average about 10 cm long and 2.5 cm wide; no fragrance detected;

Leaf color: Young adaxial between RHS 144A and RHS 138A, abaxial nearest RHS 146C; mature adaxial nearest RHS NN137B, abaxial between RHS 137B and RHS 147B;

Petiole: On basal leaves only, not on cauline leaves; concavo-convex; glabrous and slightly lustrous adaxial and abaxial, to 8 cm long and 10 mm across at base;

Petiole color: Adaxial midrib nearest RHS 145C with surrounding portion nearest RHS 145B and margin between RHS 138B and RHS 146B; abaxial midrib between RHS 146D and RHS 145B with surrounding portion nearest RHS 146D and margin nearest RHS 146B;

Veins: Anastomosing; glabrescent adaxial and pubescent to puberulent abaxial; adaxial slightly raised, abaxial midrib costate and secondary veins smooth;

Vein color: Adaxial midrib nearest RHS 146C proximally and distal midrib, primary, and secondary veins nearest RHS NN137C; abaxial midrib nearest RHS 146D proximally and distally nearest RHS 146B with primary veins nearest RHS 137B and secondary veins between RHS 137B and RHS 147B;

Inflorescence: Capitate; about 150 per plant at one time; primary inflorescence 9 cm across and 3 cm tall; comprising two outer rows of about 45 imbricate ray florets and about 300 to 400 central disk florets; individual inflorescence lasting about two weeks on or cut from plant; aspect upright;

Fragrance: Faint dirty fragrance detected;

Flowering period: Early July to early August in Michigan;

Peduncle: Strong, stiff; hispidulous to puberulent; cylindrical; fistulose; striated with ridges; 14 cm to 31 cm long and about 4 mm diameter at base; aspect upright;

Peduncle color: Between RHS 146B and RHS 146A with ridges nearest RHS 146C;

Bud: With ray florets still vertical-oblong globose; 2.6 cm across ray florets and 2.4 cm from base of phyllaries to apex of ligules;

Bud color: Adaxial and abaxial ray floret ligule nearest RHS 157A proximally, distal portion nearest RHS 155C; phyllaries nearest RHS 137C in center and margin nearest RHS 146B;

Floret type: Ray florets on the exterior two rows, disk florets in inflorescence center;

Ray florets: To about 48 per inflorescence; pistillate; arranged around outer perimeter of capitulum in two overlapping rows; ligules glabrous adaxial and abaxial, base attenuate rolled into claw, apex emarginate with typically two notches indented to about 0.5 mm, margin entire; to about 40 mm long and 11 mm wide; flat to slightly reflex in distal 4 mm;

Disk florets: Perfect; incomplete; tubular; about 300 to 400 per inflorescence in central portion of capitulum; combined inflorescences disk to about 26 mm across and about 12 mm tall; individual floret about 9 mm tall to exerted stigma and 2 mm wide; five tepals, about 5 mm long; with acute apex, fused in basal 4 mm;

Ray floret color: When ray floret are first horizontal adaxial and abaxial ligules nearest RHS NN155C, base claw nearest RHS 145A; mature adaxial and abaxial ligules between RHS NN155C and RHS NN155D, base claw between RHS 146D and RHS 145A;

Disk floret color: Young adaxial and abaxial corolla tube nearest RHS 12B in distal 1 mm, corolla tube basal 3.5 mm translucent with veins between RHS 144A and RHS 144B; mature adaxial and abaxial corolla tube nearest RHS 12B distally, center transparent and base nearest RHS 148B;

Androecium: Five stamens connate around style; on disk florets only;

*Anther*.—Five; connate into tube; about 2 mm long and less than one mm wide, not present in ray florets, functional in disk florets; color nearest RHS 14B.

*Filaments*.—Fused together at apex, 3 mm long and less than 0.1 mm diameter; color translucent to nearest RHS 145D.

*Pollen*.—Only found in disk florets; color nearest RHS 17A.

Gynoecium: In ray florets and disk florets; to about 7 mm long; exserted;

*Style*.—About 6 mm long and less than 0.3 mm diameter; color nearest RHS 9A.

*Stigma*.—Bifid; to about 1.5 mm long and less than 0.5 mm diameter; color nearest RHS 145D.

*Ovary*.—About 2.5 mm long and 1 mm wide; color nearest RHS 146D.

Involucre: Made of about two to three layers of phyllaries; to 27 mm across and 9 mm tall;

Phyllaries: About 44; lanceolate; apex acute; base truncate; imbricate; margin erosulate and translucent; adaxial and abaxial glabrous, matte; to about 9 mm long and 4 mm wide;

Phyllaries color: Adaxial and abaxial outer 1 mm of margin transparent; adaxial center nearest RHS 137B and margin nearest RHS 146C; abaxial nearest RHS 137B with a midrib nearest RHS 137A and margin nearest RHS 138A; adaxial and abaxial apex nearest RHS 200A;

Fruit: No seeds have been observed;

*Leucanthemum* 'Dream Big' grows best with adequate moisture but can tolerate some dryness once established. Vernalization is not required for flowering but is beneficial in providing uniformity and flower abundance. The new plant is tolerant of high temperatures of at least 36° and cold hardy to at least USDA zone 5 as well as strong wind and rain. Other disease or pest resistance beyond that common to Shasta daisy has not been observed.

I claim:

1. The new and distinct Shasta daisy *Leucanthemum* plant named 'Dream Big' as herein described and illustrated.

* * * * *